United States Patent [19]

Kirschbaum et al.

[11] Patent Number: 5,103,816
[45] Date of Patent: Apr. 14, 1992

[54] COMPOSITE FOR USE IN MAKING PROTECTIVE ARTICLES FOR USE IN LASER SURGERY

[75] Inventors: Warren Kirschbaum, Kemah; Steven L. Weinberg, League City, both of Tex.

[73] Assignee: Biomedical Device Consultants, Inc., League City, Tex.

[21] Appl. No.: 491,177

[22] Filed: Mar. 9, 1990

Related U.S. Application Data

[63] Continuation-in-part of Ser. No. 405,519, Sep. 11, 1989, abandoned.

[51] Int. Cl.$^5$ .................. A61M 16/00; A62B 9/06
[52] U.S. Cl. .................. 128/207.14; 128/207.15; 128/911
[58] Field of Search .................. 128/207.14, 207.15, 128/911

[56] References Cited

U.S. PATENT DOCUMENTS

| | | | |
|---|---|---|---|
| 4,377,164 | 3/1983 | Sabbota | 128/207.14 |
| 4,378,796 | 4/1983 | Milhaud | 128/207.15 |
| 4,489,722 | 12/1984 | Ferraro et al. | 128/207.15 |
| 4,601,286 | 7/1986 | Kaufmann | 128/894 |
| 4,604,998 | 8/1986 | Bellina | 128/849 |
| 4,611,588 | 9/1986 | Laptewicz, Jr. et al. | 128/846 |
| 4,616,641 | 10/1986 | Teeple | 128/846 |
| 4,632,108 | 12/1986 | Geil | 128/207.14 |
| 4,706,680 | 11/1987 | Keusch et al. | 128/640 |
| 4,834,087 | 5/1989 | Coleman et al. | 128/207.14 |

FOREIGN PATENT DOCUMENTS

| | | | |
|---|---|---|---|
| 0200292 | 11/1986 | European Pat. Off. | 128/207.15 |
| 2144639 | 3/1985 | United Kingdom | 128/207.14 |

OTHER PUBLICATIONS

Krug, P. J. et al., "Tonsillectomy and Adenoidectomy; Laser Procedures", 50 Aron Journal 990 (1989).
Bivona, Inc. (Gary, Ind.) Sales Sheet, "The Fome--Cup ® Laser Endotracheal Tube for use with $CO_2$ Lasers", (date unknown).
Sales Literature entitled "Competitive Products", source unknown (date uncertain).
Americal Corporation (Mystic, CN) Sales Materials, "Introducing Merocel ® Laser-Guard Endotracheal Tube Protector", and Directions for Application and Use of Merocel ® Laser-Guard Endotracheal Tube Protector (dates uncertain).
American V. Mueller, "Norton Endotracheal Tube", Nov. 1983, 3 pages.
"Hawley's Condensed Chemical Dictionary", 11th Ed., Sax et al., Van Nostrand Reinhold Co., N.Y. © 1987, pp. 18, 19, 519, & 932.

*Primary Examiner*—Edgar S. Burr
*Assistant Examiner*—Kimberly L. Asher
*Attorney, Agent, or Firm*—Vaden, Eickenroht, Thompson & Boulware

[57] ABSTRACT

A composite of an adhesive layer, foil, a fire retardant fabric, and a hydrogel which is used to protect objects during laser surgery and which possesses favorable burning, flashing, and resistance to burn through properties. The hydrogel is preferably a hydrophilic material such as a polyurethane, collagen, polyacrylonitrile, polyvinyl alcohol, or polyvinyl acetal. The fire retardant fabric is preferably a fabric woven or knitted from polyamide or polyimide fibers having a thickness sufficient to provide the desired degree of protection. The composite is applied to the object to be protected, which can be a person or an endotracheal tube or surgical instrument, using the adhesive to adhere the composite thereto.

11 Claims, 1 Drawing Sheet

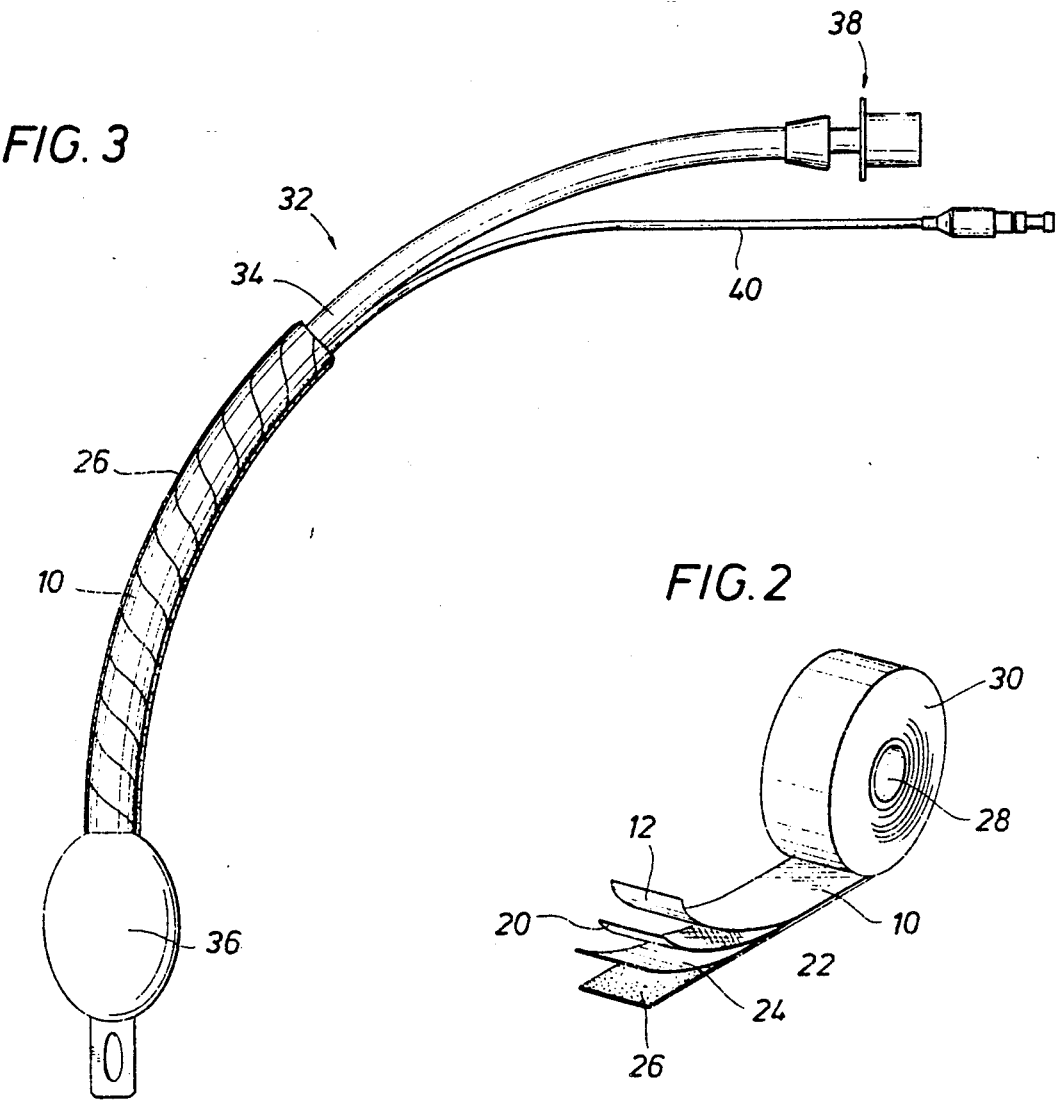
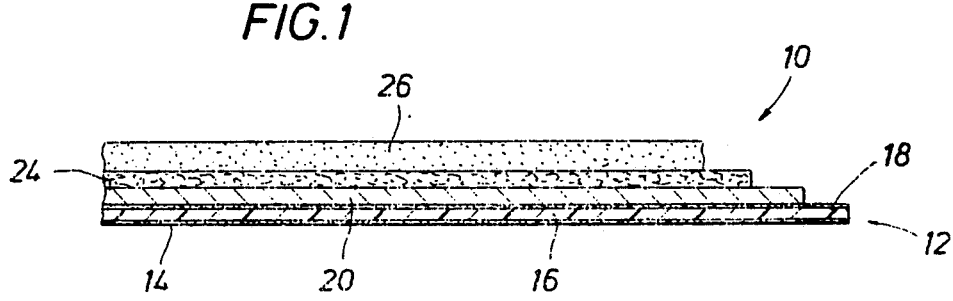

COMPOSITE FOR USE IN MAKING PROTECTIVE ARTICLES FOR USE IN LASER SURGERY

BACKGROUND OF THE INVENTION

This application is a continuation-in-part of co-pending application Ser. No. 07/405,519, filed Sep. 11, 1989, now abandoned.

The present invention relates to a composite for protection of objects, including the patient as well as surgical personnel, during laser surgery. In more detail, the present invention relates to a laser resistant composite for use in making objects such as surgical retractors, endotracheal tubes, catheters, and other items used in laser surgery for protecting both patient and surgical personnel from damaged tissue resulting from direct incidence of a laser on that object or reflected laser beams on tissue during surgery or from fire resulting from incidence of a laser on flammable materials.

Although most damage to the skin or other tissue from a laser is repairable, the extent of the damage varies depending upon the degree of absorption of the laser wavelength and the duration of exposure such that there is potential for serious damage. Adding to that potential is the fact that reflection of the laser beam is potentially as damaging as direct contact with the beam. Various safety measures are employed depending upon the surgical procedure to protect against such damage. For instance, a back drop is used behind the tissue being lased, when possible, and in the abdominal cavity, a wet wooden tongue blade, titanium rod or wet laparotomy sponge can be used to protect underlying tissue. Abdominal and cranial cavities are filled with sterile saline to absorb the energy of the beam. Non-involved, exposed tissue is covered with wet laparotomy sponges, four by fours, or cottonoids. Patients are restrained from movement, and beaded or other non-reflective instruments are used.

Fires can occur by ignition of a drape, endotracheal tube, or article of clothing, plastic, or rubber in the treatment area. On information and belief, none of the standard surgical drapes will resist impact from a laser beam. Precautions against fire include, for instance, the covering of surgical drapes with wet towels and/or laparotomy sponges, the wetting of all the drapes, sponges and gauzes used in the area of laser application, and the precautions listed above for protecting against laser burns. A more complete listing of these precautions is set out in the report of the Technical Practices Coordinating Committee of the Association of Operating Room Nurses, published as Recommended Practices—Laser Safety in the Practice Setting, 50 AORN J. 1015-1020 (Nov. 1989) and in Safety Issues in Clinical Laser Management, published by Clinical Laser Monthly (Feb. 1990).

A particularly dangerous fire problem is presented by the use of an endotracheal or nasotracheal tube for management of a patient during, for instance, an ENT procedure with a laser. To some extent, the problem exists with any procedure involving the use of a laser in the vicinity of a catheter or other disposable plastic or rubber surgical products, but in the case of an endotracheal tube, the tube is filled with pure oxygen such that the likelihood of fire is greatly increased. Polyvinyl chloride (PVC) and red rubber endotracheal tubes can melt upon exposure to laser beams, causing patient tissue burning, and metal and other flexible tubes can crack, causing fire when escaping oxygen ignites. Metal tubes are available which do not melt or burn, but they can block the surgeon's view, often are not as flexible as plastic or rubber tubes and may be larger in diameter thereby increasing the difficulty of inserting the tube, and can reflect the laser beam. In the case of large patients, the smaller internal diameter of flexible metal endotracheal tubes presents problems in providing adequate ventilation for the patient. It is known to wrap a rubber or PVC endotracheal tube with aluminum or other metal tape, but wrapped tubes are more difficult to insert, the ragged edges of the tape can damage the airway, the tape provides little protection against penetration of a laser beam, and the tape is laser reflective such that there is the possibility of damage or even fire from a reflected laser beam.

In short, the protection provided by even the most careful application of all of these precautions simply is not sufficient, and the precautions themselves give rise to certain inconveniences as listed. Depending upon the wavelength, time of exposure, type of laser and several other factors, the laser is capable of vaporizing these "protective" articles in exactly the same manner as the tissue on which the laser is intended to be used. There is, therefore, a need for a way to protect various objects such as surgical instruments, patients and surgical personnel in the treatment area.

Attempts have been made to provide an article which can be so used. U.S. Pat. No. 4,601,286 is directed to an "Article for the Protection of Living Tissues", said to protect ". . . living tissue from damage due to exposure to lasers . . . ". That patent describes the use of a hydrogel in the form of a drape or dressing having an opening through which the laser light can pass to impinge on the portion of the tissue to be lased, the opening having a size and shape approximating that of the tissue site to be lased (col. 5, lines 13-20, 56-60). In practice, however, such an article does not protect against laser burns; at best, such articles may provide some protection against ignition because of the high water content of the hydrogel. Experimentation has shown that penetration of a twenty-five watt or greater laser through such articles is instantaneous; further, the hydrogels are clear, making them of limited use for argon lasers which "seek" color. Penetration of the laser through the hydrogel does not appear to depend on the thickness of the hydrogel—instead, the laser penetrates instantaneously no matter what the thickness.

Similarly, a laminate is available under the trademark MEROCEL LASER-GUARD from Americal Corporation (Mystic, Conn.) which is applied to an endotracheal tube, ostensibly for the purpose of protecting that endotracheal tube from damage by an incident laser beam. According to that company's promotional literature, that product is comprised of a 1 mm thick MEROCEL sponge portion which, on information and belief, is a hydrogel composed of a polyvinyl alcohol, and a 1 mil metal foil laminated to each other by "a special waterproof hypoallergenic adhesive". Although the promotional literature for that product indicates that the laminate is capable of withstanding incident laser beams for up to 90 seconds, experimentation has shown that such claims may be somewhat optimistic. Further, that product, when applied to rubber or some PVC endotracheal tubes, decreases the flexibility of the endotracheal tube because it is supplied as a long rectangular patch into which the tube portion of the endotracheal tube is rolled. As noted above, the flexibility of the tube is important because stiffer tubes are more difficult to insert.

There is, therefore, still a need for a material which can be applied to an object such as an endotracheal tube to provide effective protection from an incident laser beam. There is also a need to which the two approaches summarized have not even attempted to respond, namely, the need for protecting objects such as retractor blades, endoscopes, specula, and other objects used during laser surgical procedures from damage by exposure to the laser beam, and to protect living objects (the patient and surgical personnel) from reflected laser beams.

SUMMARY OF THE INVENTION

The present invention satisfies that need by providing a laser resistant composite for application to an object to be protected from damage from an incident laser beam. The object can be a surgical instrument, catheter, endoscope, or endotracheal tube, or the object can be the patient or the attending surgical team and/or portions of the bodies or clothing of such persons. The composite comprises an adhesive backed foil, a layer of fire retardant fabric bonded to the foil on the side opposite the adhesive, and a hydrogel, acting as an insulative layer, laminated to the fire retardant fabric. The adhesive may be any material which is more cohesive than adhesive to the surface to be protected and which is mechanically connected more firmly to the foil than affixed to the plastic or metal of the surgical instrument or other object such as skin or a tissue surface to be protected. The hydrogel/insulative layer is preferably water insoluble or hydrophilic. The fire retardant fabric is a fabric comprised of woven, knitted, or braided fabric, or a non-woven or random dispersion of polyamide, polyimide, carbon, quartz, silica, ceramic, or other fibers, which is able to withstand exposure to heat and/or flame, as well as those fabrics which have been treated by application of a finish that cuts off the oxygen supply around a flame. Such a composite is supplied in sheets which are cut and applied to, for instance, a retractor or speculum blade, endotracheal or nasotracheal tube, or catheter, an internal organ or the eyes of the patient, or other object, including portions of the anatomy of the patient or surgical personnel and/or their glove(s) or other clothing, before laser surgery and, if necessary, trimmed to size.

In a preferred embodiment, such a composite is made in a strip which is wound around the tube portion of an endotracheal tube for protecting the endotracheal tube from damage caused by an incident laser beam. The strip is wound around the tube in spiral, or "barber pole" fashion so as not to decrease the flexibility of the tube. The composite can also be supplied in various pre-cut shapes and applied to the surface of objects such as retractor blades, and trimmed to size, to prevent reflection of the laser beam.

DETAILED DESCRIPTION OF THE PREFERRED EMBODIMENTS

As used herein, the phrase "adhesive layer" refers to any material which is more cohesive than adhesive to the surface to be protected from laser damage and/or burn and which is mechanically connected more firmly to the foil than to the surface to be protected. Appropriate adhesives are well known in the art, and include any waterproof and/or water resistant, hypoallergenic adhesive such as an acrylic adhesive and those available from 3M (St. Paul, Minn). In one embodiment, the adhesive layer is a hydrogel. After the adhesive is applied to the foil, that two-layer structure is referred to herein as "adhesive-backed foil".

The layer of hydrogel provides insulation from the heat of an incident laser beam as described below. The hydrogels may be specifically a polyurethane; polyacrylonitrile; polymer of acrylic acid, methacrylic acid, ethacrylic acid, alpha-chloracrylic acid, alpha-cyanoacrylic acid, beta-methylacrylic acid (crotonic acid), alpha-phenyl acrylic acid, beta-acryloxypropionic acid, sorbic acid, angelic acid, cinnamic acid, itaconic acid, maleic acid, fumaric acid, tricarboxyethylene, maleic anhydride, vinylsulfonic acid, allyl sulfonic acid, acrylic and methacrylic sulfonic acid, sulfoethyl acrylate, and methacrylate; block polymers of poly(ethylene oxide); acrylonitrile-acrylamide copolymers; polyhydroxyalkylmethacrylates; polyacrylamide; polymethylamide; poly(N-vinyl-2-pyrrolidone); polyvinyl alcohol; hydroxylated polyvinyl alcohol; polyvinyl acetates; polyvinyl acetals; collagen; and co-polymers of styrene, ethylene, propylene, butylene, or isobutylene with maleic or fumaric anhydride. Those hydrogels available under the trademarks HYPAN (Kingston Technologies, Dayton, N.J.), HYPOL and BIOPOL (W. R. Grace & Co.) and VIGILON (Nepara Chemical Co., Harrison, N.Y.) are particularly preferred for use in connection with the composite of the present invention.

In addition to the high water content of the hydrogel, which helps prevent ignition of objects which are comprised of flammable materials to which the composite of the present invention is applied, the hydrogel insulates against the heat produced by the incident laser beam. Any of the hydrogels listed above may be used to advantage as the insulative layer in connection with the composite of the present invention as long as they are not themselves flammable or do not give off a significant quantity of toxic fumes or other by-products upon exposure to heat or flame.

As used herein, the phrase "fire retardant fabric" refers to any high temperature resistant or fire retardant woven, knitted, braided, non-woven, or random dispersion of fibers which can be laminated to the hydrogel and bonded to the adhesive backed foil to form the composite of the present invention and which, upon exposure to heat or flame, does not give off a significant quantity of toxic fumes or by-products. Suitable fibers are nylon, polyamide (especially aramid), polyimide, carbon, quartz, fused or leached silica, ceramic, and polybenzimidazole (PBI) fibers such as are sold in fabric form under the trademarks NOMEX (E. I. du Pont de Nemours & Co.), KEVLAR (E. I. duPont de Nemours & Co.), NEXTEL (3-M Company, St. Paul, Minn.), the KC series of uncoated aramid fabrics available from Bentley-Harris (Lionville, Pa.), Bentley-Harris KKD.1200 ceramic cloth, Bentley-Harris GKP 1106 and 1306 "Thermoshield"-treated fiberglass fabric, the Bentley-Harris GKPG range air textured glass fabrics, and UPJOHN 20-80. Suitable fire retardant fabrics also include those fabrics to which a fire retardant treatment has been applied such as treatment with an inorganic salt of ammonium sulfamate, zinc borate, or antimony oxychloride, chlorinated organic compounds such as chlorendic anhydride, alumina trihydrate, and certain organic phosphates and phosphonates, as well as those fabrics made from polymers to which a flame retardant chemical is chemically linked. An example of the latter is the polyester fiber sold under the trademark TREVIRA (Hoechst Fibers Industries) which, on information and belief, is a polymer of polyethylene terephthlate. The fabrics made from aramid fibers such as those sold under the trademarks NOMEX and KEVLAR are particularly preferred fire retardant fabrics for use in the composite of the present invention.

By the use of the term "laminated" herein, it is intended to refer to the joining of the hydrogel/insulative layer and the fire retardant fabric in such a manner as to insure the adherence of the hydrogel/insulative layer to the fire retardant fabric so that the composite of the present invention can be removed from the surface of the object which is intended to be protected, e.g., retractor blades, specula, endoscopes, etc. if desired. In one presently preferred embodiment, this lamination is accomplished by embedding a layer of fire retardant fabric into a layer of a suitable hydrogel as described above. Embedding the fire retardant fabric into the hydrogel is accomplished, for instance, by applying pressure to the fabric and hydrogel after laying one on top of the other between two flat surfaces. In the case of catheters, nasotracheal tubes, and endotracheal tubes, a convenient method of laminating the hydrogel to the fabric is to wrap the tube with an adhesive/foil/fire retardant fabric strip and then laminate the fabric and hydrogel.

Two layers of fabric can be embedded into two hydrogel/insulative layers as follows. Many hydrogels, because of their capacity for adherence, are supplied packaged between sheets of, for instance, polyethylene film. Such a three-layer package (polyethylene/hydrogel/polyethylene) is preferably laid on a flat surface and the top layer of film is pulled off of the hydrogel. Two layers of the fire retardant fabric (or fabrics) are then laid on a portion of the hydrogel and the reminder of the hydrogel folded over both layers of the fabric. Pressure is then applied and, because the hydrogel permeates the spaces between fibers of the fabric, the result is two hydrogel/fabric laminates from which the original, remaining sheet of polyethylene film can be peeled, the film providing a convenient way to handle the laminate until the laminate is bonded to the foil. As will be set out below, the same result is accomplished using a pre-bonded foil/fabric such that the result is two foil/fabric/hydrogel laminates to which an adhesive is applied.

Another preferred method for laminating the fabric to the hydrogel is to form the hydrogel in the shape of a tube, with or without the foil and fabric layers, into which the endotracheal or other tube is inserted. The adhesion of the tube to the composite of the present invention is then accomplished by hydrating the hydrogel/insulative layer by wetting the hydrogel, the swelling of the gel preventing relative movement between the composite and the endotracheal or other tube. Another embodiment illustrates the advantageous use of a hydrogel as the adhesive layer: the endotracheal or other tube is inserted into a tube formed of a hydrogel (adhesive layer)/foil/fire retardant fabric/hydrogel (insulative layer) and when water or other aqueous solution (e.g., an aqueous topical anesthetic) is added, not only is the entire assembly made moist and relatively slippery (facilitating insertion of the tube), but the hydrogel (adhesive layer) swells into such tight engagement with the endotracheal or other tube that the composite of the present invention is effectively adhered to that tube. Similarly, the fire retardant fabric can be knitted, braided, or woven in the shape of a tube, slipped over the endotracheal or other tube, and the hydrogel poured over the tube of fabric and cross-linked. The hydrogel/insulative layer is also laminated to the fire retardant fabric by embedding the fire retardant fabric into the hydrogel prior to cross-linking (e.g., addition of water), thus creating an integral structure to which the foil is bonded.

The foil is preferably a metallic foil such as aluminum, copper, silver, or stainless steel foil, and may or may not be corrugated. In a particularly preferred embodiment, the foil and the fire retardant fabric are bonded to each other when purchased. Such products as Bentley-Harris AKA 327, which is a herringbone woven fabric from that company's TBA FORTAMID range of fire retardant fabrics that has been aluminized with highly reflective GEMINI film are particularly preferred because the composite of the present invention is then conveniently manufactured by applying, for instance, a double-sided tape to the foil and laminating the insulative layer to the fire retardant fabric by pressure as described above. There are a number of double sided, pressure-sensitive tapes which are appropriate for use in this manner; a particularly preferred tape is obtained from the Health Care Specialties Division, 3M Health Care Group (St. Paul, Minn.), Product Specification Nos. 1509, 1512, 1513, 1522 and 9873. In addition to the adhesives described above, other adhesives may also be used to advantage, including the use of a hydrophilic polymer and "releasable" adhesive layers comprised of adhesives such as those available from 3M Company (St. Paul, Minn.) on one side of the fire retardant fabric. Both embodiments exhibit the capability of an adhesive layer which is mechanically connected, e.g., bonded, more firmly to the foil than to the skin or other tissue, plastic or metal to which the composite is applied.

As a general rule, it is preferred to use fire retardant fabrics which are relatively thick or dense (as that term is explained below). The resistance of the composite to the present invention to burn through by a laser is directly related to increasing thickness or density for a particular weave and type of fabric. Particular success has also been achieved by doubling and tripling the fire retardant fabric in the fabric layer and by the use of more than one type of fabric, thereby achieving the protective thickness desired without the need for using more expensive fire retardant fabrics woven in a thick weave, for instance a pile weave. However, if desired, such thicknesses can be obtained by using single and double velour, terry, or cut weaves, or by a weft or warp knit fabric.

Resistance to burn through is also improved by what might be termed "the density" of the fire retardant fabric, although changes in thickness demonstrated a greater effect on resistance than changes in density. By density, it is intended to refer to the use of coarser yarns, higher yarn counts, or tighter weaves e.g., increases in the weight of the fabric (as may be measured in, for instance, ounces per yard of fabric); in the case of non-woven and/or random dispersion fire retardant fabrics, use of the term density refers to fabrics having a higher ratio of fibers to binder.

The following experiments conducted with the presently preferred composites are illustrative of the protection which can be achieved in accordance with the teachings of the present invention. Several composites were constructed and tested for resistance to burn through as follows.

In a first test, a composite was constructed of the above described AKA 327 foil-backed FORTAMID fire retardant fabric and laminated to HYPAN (Kingston Technologies, Dayton, N.J.) hydrogel as an insulative layer. With a $CO_2$ laser at 35 watts, a 90° angle of incidence, and a 0.2 mm beam diameter, that composite resisted burn through for between 4 and 5 seconds.

In a second test, that same foil-backed fire retardant fabric was laminated to a second layer of fire retardant fabric, specifically, du Pont KEVLAR 440, and an insulative layer, in the form of the same HYPAN hydrogel was laminated to that double-layer composite. When tested with a 0.2 mm $CO_2$ laser beam at 35 watts at a 90° angle of incidence, the test was discontinued after 25 seconds with no visible sign of laser burn through.

In a third test, a Mallinckrodt 7.0 mm I.D. No. 86450 endotracheal tube was wrapped with a composite comprised of the above-described 3M double-sided tape and Bentley Harris AKA 327 foil/fabric, and then an insulative layer, specifically the HYPAN hydrogel listed above, was laminated to the tube by crosslinking the gel to the fire retardant fabric of the adhesive/foil/fabric-wrapped endotracheal tube by wetting a hydrogel that was poured over the wrapped tube. When tested with a 0.2 mm $CO_2$ laser beam at 35 watts and a 90° angle of incidence, the wrapped tube resisted burn through for between 4 and 5 seconds.

BRIEF DESCRIPTION OF THE DRAWINGS

FIG. 1 shows a cross-section through a composite in accordance with the present invention.

FIG. 2 shows the composite in the form of an elongate strip which is wound on a spool into a roll.

FIG. 3 shows an endotracheal tube wrapped with the composite.

Referring now to the figures, a cross-section through a composite in accordance with the present invention is indicated generally at reference numeral 10 in FIG. 1. The composite 10 is comprised of an adhesive in the form of a double layer, pressure sensitive tape, shown generally in FIG. 1 at reference numeral 12. Tape 12 includes a layer of adhesive 14, a second layer of adhesive 18, and the film 16 to which adhesive layers 14 and 18 are applied, the second layer of adhesive 18 acting to adhere the tape 12 to the layer of foil 20, e.g., the adhesive-backed foil. As shown in FIG. 2, the foil 20 is corrugated as at reference numeral 22, but as noted above, need not be corrugated to be appropriate for use in connection with the present invention. Foil 20 is bonded to a layer of fire retardant fabric 24, and a hydrogel/insulative layer 26 is laminated to the fabric 24. The composite 10, as shown in FIG. 2, can be supplied in the form of an elongate strip which is wound on a spool 28 into a roll 30.

An endotracheal tube made laser resistant by application of the composite 10 thereof is shown in FIG. 3. As known in the art, the endotracheal tube 32 is comprised of a tube 34, inflatable cuff 36, tube 38 for inflating the cuff 36, and connector 40. The strip of composite 10 is applied to the tube 34 of endotracheal tube 32 by wrapping the strip around the tube 32 in spiral, or "barber-pole" fashion, using the adhesive layer 14 of the tape 12 to adhere the composite 10 to the surface of the tube 34. As noted above, the hydrogel/insulative layer 26 can also be laminated to the wrapped endotracheal tube 32 after a composite of adhesive-backed foil/fire retardant fabric is wrapped around the tube 34 thereof. The external appearance of such an endotracheal tube is the same as shown in FIG. 3. In either method of application, when wrapped around the tube 34 in this manner, the hydrogel 26 is outermost, providing a moist surface which facilitates insertion of the endotracheal tube 32 by reducing the potential for trauma and easing the insertion of the tube into the patient's airway. If desired, the hydrogel provides a convenient vehicle for application of an aqueous solution of a topical anesthetic as described above. Either way, the patient's airway is not damaged.

Having described these presently preferred embodiments as being exemplary of the present invention as required by §112 of the Patent Statute, it is not intended that the scope of the present invention be so limited. Those skilled in the art who have the benefit of this disclosure will recognize, for instance, that there are fire retardant fabrics other than those listed above which may be used to advantage in the composite of the present invention. Likewise, adhesives other than those described herein may be suitable for use as the adhesive layer of the composite of the present invention. All such changes and/or variations are intended to fall within the scope of the following claims.

What is claimed is:

1. An endotracheal tube which resists exposure to an incident laser beam comprising an endotracheal tube and a laser resistant composite, said laser resistant composite being applied to said endotracheal tube by wrapping around the tube, said laser resistant composite being comprised of
   an adhesive backed foil;
   a layer of fabric bonded to said foil on the side opposite the adhesive, the layer of fabric being fire retardant in that the fabric comprising the layer of fabric does not burn wet or dry, when exposed to a source of heat or flame; and
   an insulative layer laminated to the layer of fabric.

2. The endotracheal tube of claim 1 wherein said fire retardant fabric is comprised of polyamide fibers.

3. The endotracheal tube of claim 1 wherein the adhesive of said adhesive-backed foil is a hydrogel.

4. The endotracheal tube of claim 1 wherein said insulative layer is a hydrogel.

5. The endotracheal tube of claim 4 additionally comprising an aqueous solution of a topical anesthetic, said hydrogel providing a vehicle for application of said anesthetic.

6. The endotracheal tube of claim 1 wherein the foil of said adhesive-backed foil is corrugated.

7. A laser resistant tube for inserting into a patient during a surgical procedure involving the use of a laser comprising:
   a non-metallic tube for insertion into a patient;
   a metallic foil;
   a layer of fire retardant fabric bonded to said foil;
   an insulative layer of hydrogel laminated to said layer of fire retardant fabric; and
   an adhesive layer between said tube and said metallic foil for adhering said metallic foil thereto whereby said insulative layer of hydrogel is outermost for providing a moist surface which facilitates insertion into the patient, said fire retardant fabric being resistant to burning upon exposure to an incident laser beam with or without said layer of moist hydrogel being laminated thereto.

8. The laser resistant tube of claim 7 wherein said adhesive layer comprises a hydrogel.

9. The layer resistant tube of claim 8 wherein said insulative layer comprises a hydrogel.

10. The laser resistant tube of claim 8 additionally comprising a topical anesthetic in said insulative layer.

11. The laser resistant tube of claim 8 wherein said metallic foil is corrugated.

* * * * *